(12) United States Patent
Hogendijk

(10) Patent No.: US 7,004,931 B2
(45) Date of Patent: Feb. 28, 2006

(54) PROXIMAL CATHETER ASSEMBLY HAVING A SELF-LIMITING ASPIRATION VALVE

(75) Inventor: Michael Hogendijk, Palo Alto, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 200 days.

(21) Appl. No.: 10/278,101

(22) Filed: Oct. 21, 2002

(65) Prior Publication Data
US 2003/0187391 A1 Oct. 2, 2003

Related U.S. Application Data

(63) Continuation-in-part of application No. 10/138,013, filed on May 1, 2002, which is a continuation-in-part of application No. 10/112,807, filed on Mar. 29, 2002.

(51) Int. Cl.
*A61M 5/00* (2006.01)
*A61M 1/00* (2006.01)

(52) U.S. Cl. .................................. 604/247; 604/129

(58) Field of Classification Search .................. 604/35, 604/118, 119, 121, 246–250, 129, 500
See application file for complete search history.

(56) References Cited

U.S. PATENT DOCUMENTS

| | | | |
|---|---|---|---|
| 4,230,128 A | 10/1980 | Aramayo | 128/763 |
| 4,310,017 A | 1/1982 | Raines | 137/533 |
| 4,397,335 A | 8/1983 | Doblar et al. | 137/625.19 |
| 4,510,933 A * | 4/1985 | Wendt et al. | 128/207.14 |
| 4,595,005 A | 6/1986 | Jinotti | 128/205.24 |
| 4,642,097 A | 2/1987 | Siposs | 604/119 |
| 4,668,215 A | 5/1987 | Allgood | 604/30 |
| 4,680,026 A | 7/1987 | Weightman et al. | 604/33 |
| 4,708,717 A | 11/1987 | Deane et al. | 604/35 |
| 4,850,350 A | 7/1989 | Jackson | 128/207.16 |
| 4,921,478 A | 5/1990 | Solano et al. | 604/53 |
| 4,957,482 A | 9/1990 | Shiber | 604/22 |
| 4,964,849 A | 10/1990 | Robicsek | 604/35 |
| 5,034,000 A | 7/1991 | Freitas et al. | 604/30 |
| 5,135,492 A | 8/1992 | Melker et al. | 604/53 |
| 5,203,769 A | 4/1993 | Clement et al. | 604/32 |
| 5,230,704 A | 7/1993 | Moberg et al. | 604/34 |
| 5,250,060 A | 10/1993 | Carbo et al. | 606/159 |
| 5,269,768 A | 12/1993 | Cheung | 604/248 |
| 5,453,097 A | 9/1995 | Paradis | 604/247 |
| 5,484,412 A | 1/1996 | Pierpont | 604/101 |
| 5,496,270 A | 3/1996 | Nettekoven | 604/30 |
| 5,707,356 A | 1/1998 | Paul | 604/119 |
| 5,833,650 A | 11/1998 | Imran | 604/53 |
| 5,902,264 A | 5/1999 | Toso et al. | 604/27 |
| 5,919,174 A | 7/1999 | Hanson | 604/283 |

(Continued)

*Primary Examiner*—Sharon Kennedy
(74) *Attorney, Agent, or Firm*—Kevin J. Boland

(57) ABSTRACT

The present invention is directed to a proximal catheter assembly configured to facilitate natural or suction-assisted aspiration through a catheter lumen. The proximal catheter assembly comprises a multi-function valve configured to perform functions associated with conventional check valves and relief valves. The valve is configured to regulate the direction of fluid flow, and further configured to regulate the rate of suction-assisted aspiration provided through the lumen of the catheter. When the rate of suction-assisted aspiration exceeds a predetermined threshold, the valve opens to allow fluid to be drawn from tubing coupled to the proximal catheter assembly, thereby mitigating excessively high rates of aspiration imposed upon the patient's vessel.

22 Claims, 8 Drawing Sheets

U.S. PATENT DOCUMENTS

| | | |
|---|---|---|
| 6,022,336 A | 2/2000 | Zadno-Azizi et al. .......... 604/96 |
| 6,142,980 A | 11/2000 | Schalk ....................... 604/247 |
| 6,168,577 B1 | 1/2001 | Niederjohn et al. .......... 604/23 |
| 6,482,217 B1 | 11/2002 | Pintor et al. ................. 606/159 |
| 6,712,815 B1 * | 3/2004 | Sampson et al. ............. 606/41 |
| 2002/0052638 A1 | 5/2002 | Zadoo-Azizi ............... 623/1.2 |

* cited by examiner

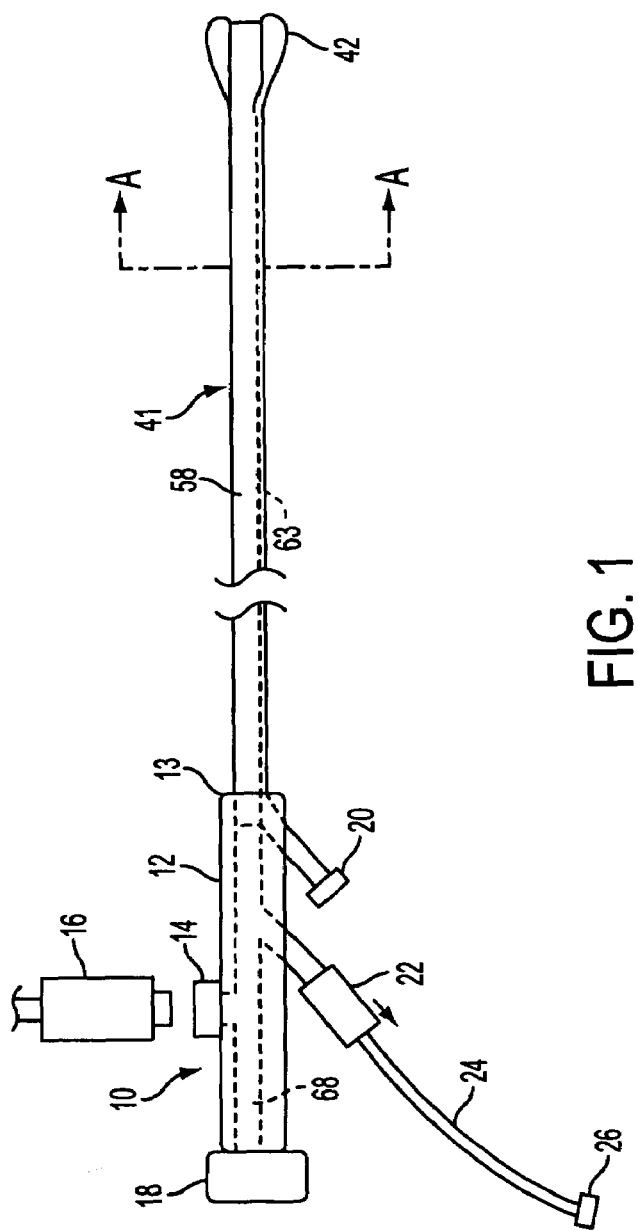
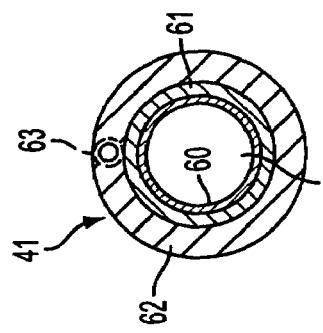
FIG. 1
FIG. 2

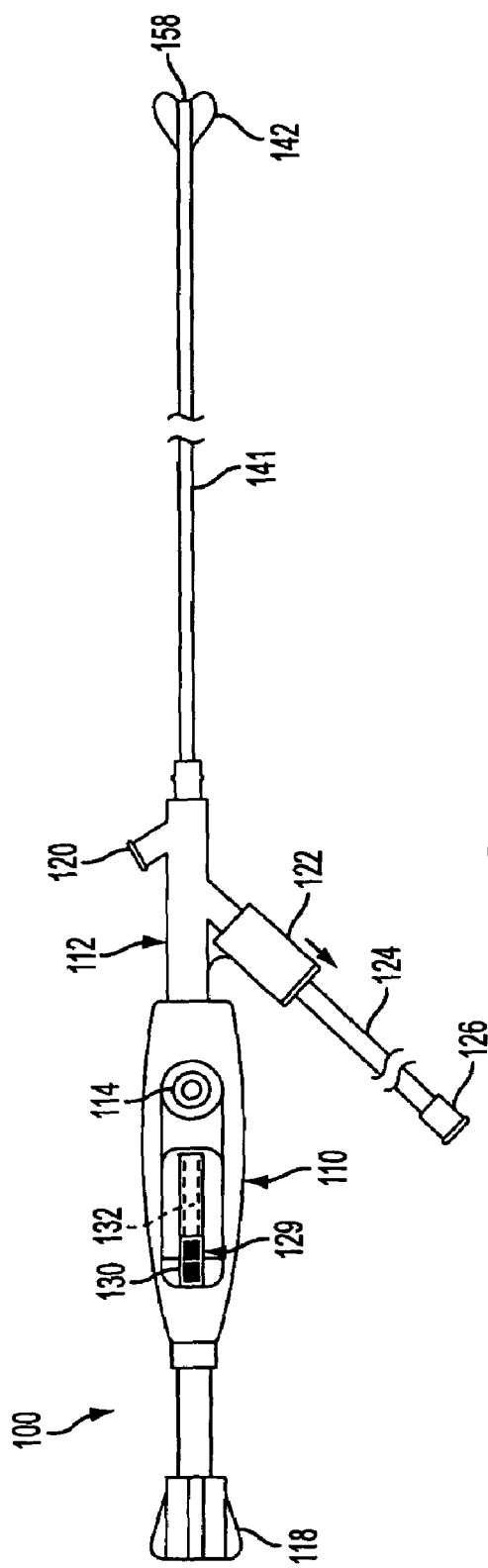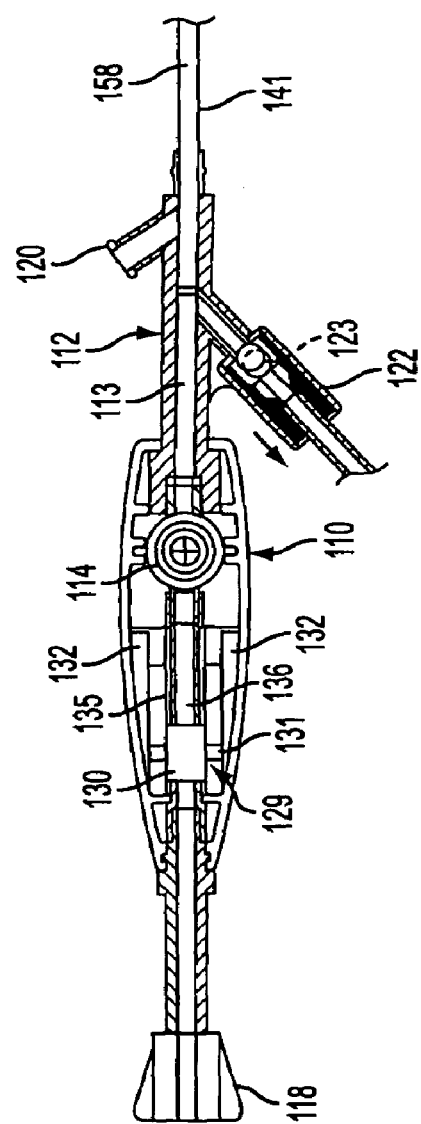
FIG. 3A
FIG. 3B

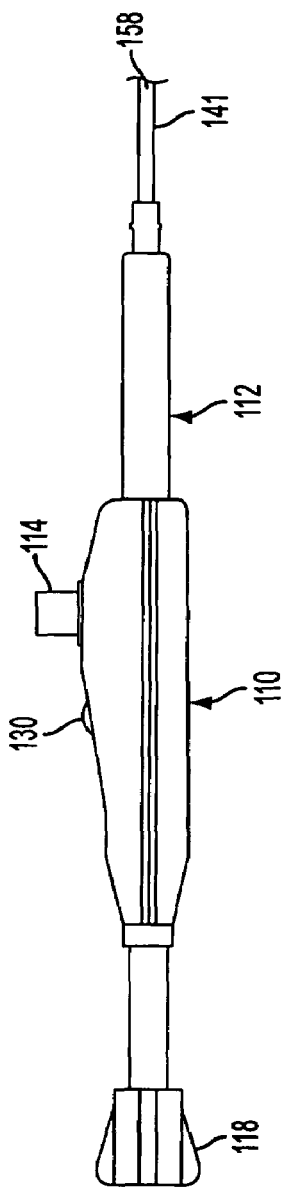
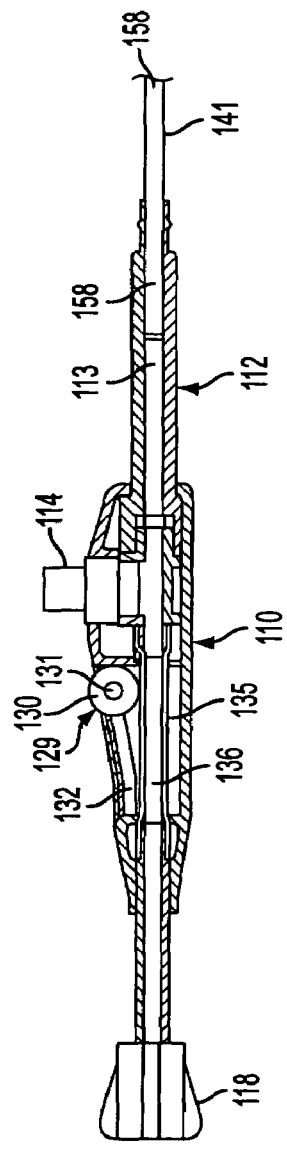
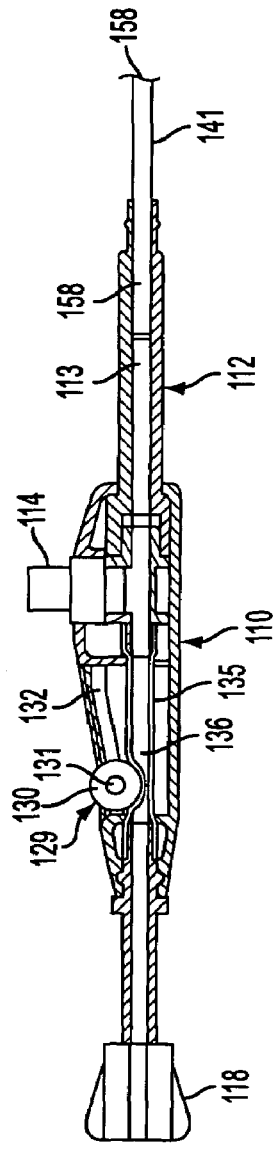

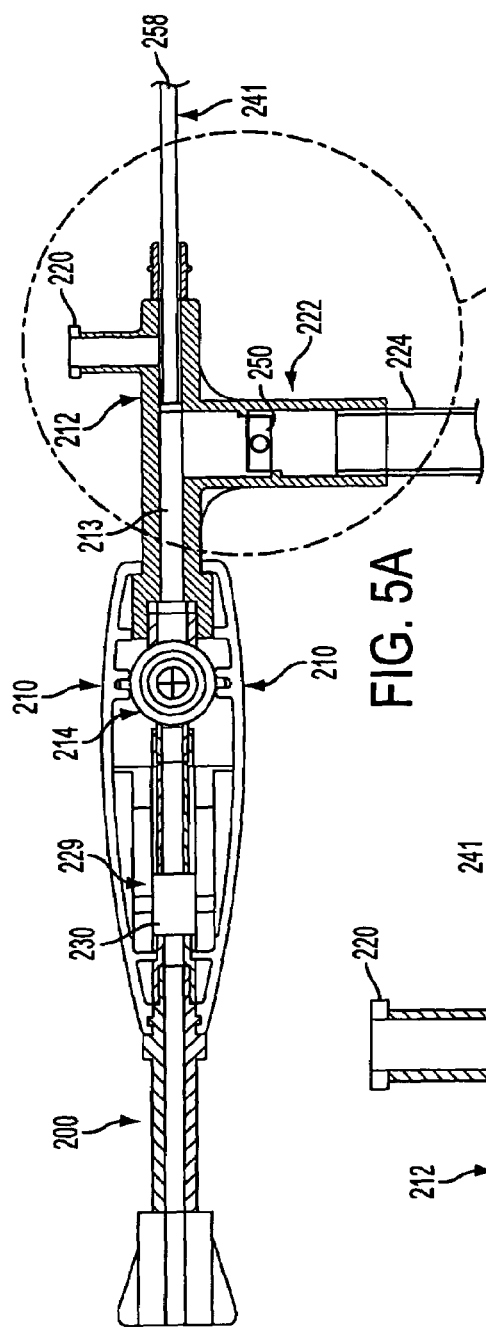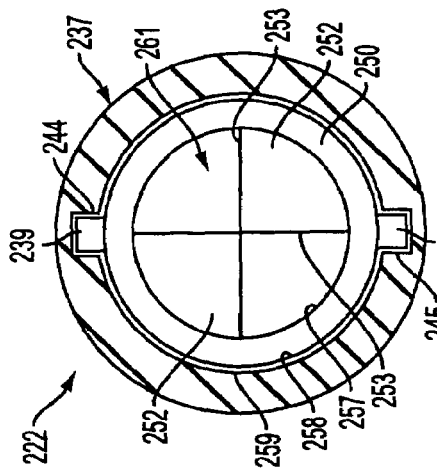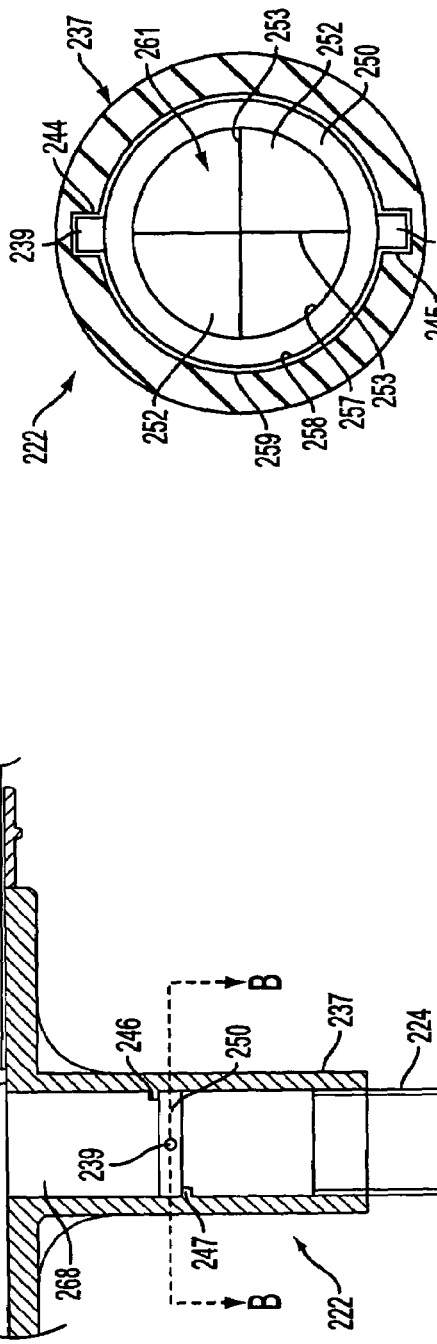

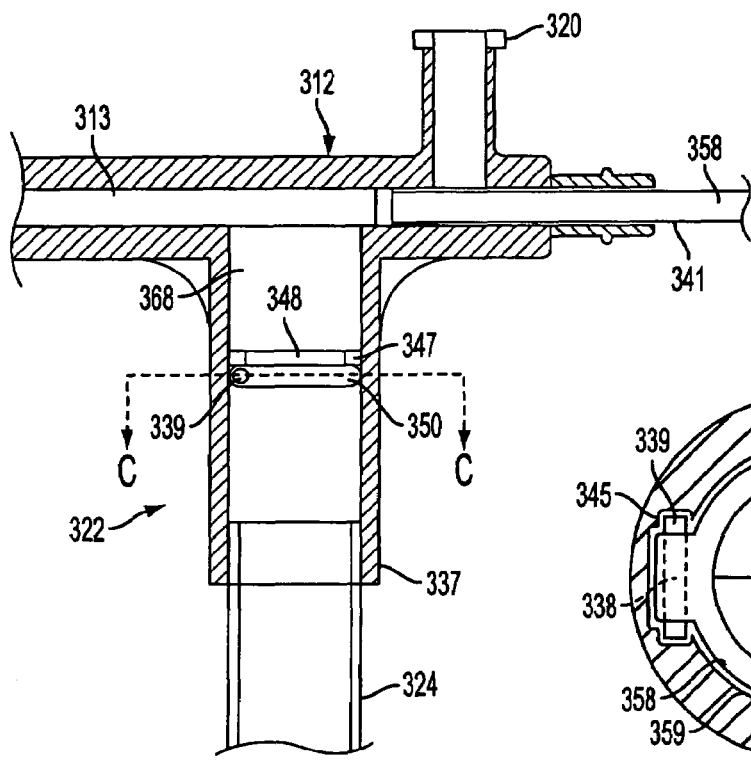
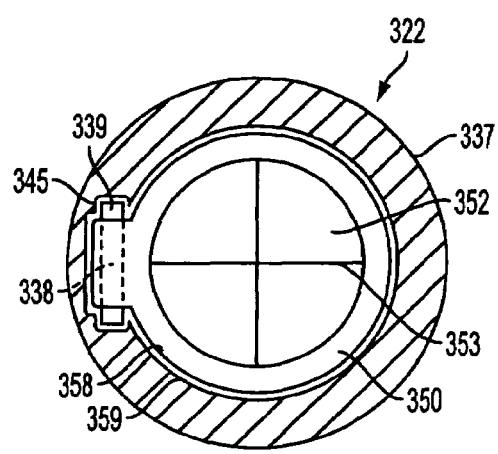
FIG. 7A
FIG. 7B
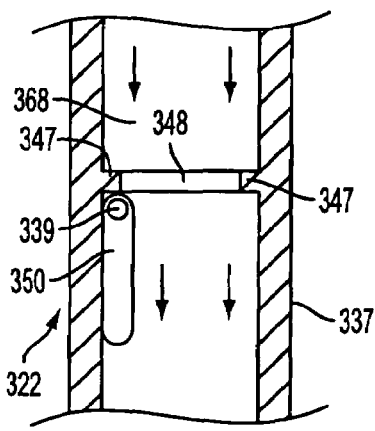
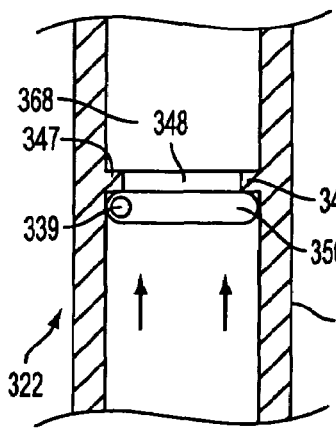
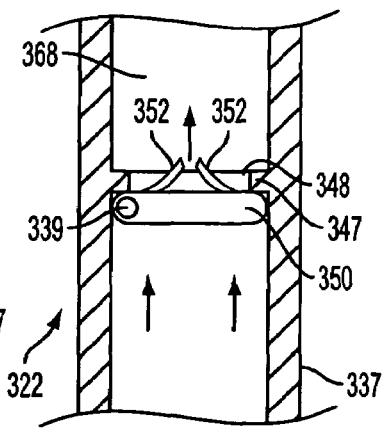
FIG. 8A
FIG. 8B
FIG. 8C

PROXIMAL CATHETER ASSEMBLY HAVING A SELF-LIMITING ASPIRATION VALVE

REFERENCE TO RELATED APPLICATIONS

The present application is a continuation-in-part of U.S. patent application Ser. No. 10/138,013, filed May 1, 2002, which is a continuation-in-part of U.S. patent application Ser. No. 10/112,807, filed Mar. 29, 2002.

FIELD OF THE INVENTION

The present invention relates to an improved proximal catheter assembly, and more specifically, a catheter handle that is configured to provide a lumen of a catheter with substantially continuous natural aspiration and, optionally, suction-assisted aspiration that may be regulated using a self-limiting valve.

BACKGROUND OF THE INVENTION

Today there is a growing need to provide controlled access and vessel management during such procedures as stenting, atherectomy or angioplasty. Generally, during these procedures there is a high risk for the release of embolic material. The emboli may travel downstream from the occlusion, lodging deep within the vascular bed and causing ischemia. The resulting ischemia may pose a serious threat to the health or life of a patient if the blockage forms in a critical area, such as the heart, lungs, or brain.

Several previously known methods and apparatus incorporate the use of an external suction system in conjunction with an aspiration catheter for removal of the clot and/or removal of embolic particles. However, several disadvantages arise when using an external suction system as the sole means for flow management within a vessel. First, it may be difficult to establish the proper aspirating pressure required at the treatment site, and external pressure adjustments used with suction pumps may lead to an incorrect amount of suction for a given set of circumstances. If the amount of suction is too low for the circumstances, then embolic particles may not be effectively removed and may travel downstream from the original occlusion, leading to further occlusive events. If the amount of suction is too high, the vessel may collapse.

Moreover, if an external suction pump is utilized, retrieval of downstream emboli may require a flow rate that cannot be sustained by the vessel wall for more than a few seconds, resulting in insufficient removal of emboli. Additionally, continuous use of an external suction pump may result in excessive blood loss, requiring infusion of non-autologous blood and raising related safety issues.

Other methods for embolic removal have relied on more natural aspirating effects. For example, previously known devices have relied on the pressure differential between the atmosphere and blood flow in a treatment vessel to cause a reversal of flow in the treatment vessel. However, such natural aspiration techniques may provide insufficient flow to effectively remove emboli.

In view of these drawbacks of previously known systems, it would be desirable to provide a proximal catheter assembly that allows a catheter to achieve a substantially continuous level of natural, physiologically-regulated aspiration through a working lumen of the catheter.

It also would be desirable to provide a proximal catheter assembly that provides an appropriate level of retrograde flow at a treatment site to direct dislodged particles into a catheter for efficient removal without damaging the treatment vessel.

It further would be desirable to provide a proximal catheter assembly that provides an external suction/infusion port that selectively may be used, in conjunction with natural aspiration techniques, to further influence flow in a treatment vessel.

It still further would be desirable to provide a proximal catheter assembly that allows emboli to be filtered and blood reperfused into a patient's vessel to reduce blood loss.

It yet further would be desirable to provide a proximal catheter assembly that is configured to minimize "back-bleed" that occurs when flow exits through a hemostatic port disposed at the proximal end of a catheter.

It also would be desirable to provide a proximal catheter assembly having a check valve functionality to selectively enable the provision of either natural or suction assisted aspiration through a working lumen of a catheter.

It also would be desirable to provide a proximal catheter assembly having a relief valve functionality to regulate the level of suction-assisted aspiration that may be provided through the working lumen of the catheter.

SUMMARY OF THE INVENTION

In view of the foregoing, it is an object of the present invention to provide a proximal catheter assembly that allows a catheter to achieve a substantially continuous rate of natural, physiologically-regulated aspiration through a working lumen of the catheter.

It is also an object of the present invention to provide a proximal catheter assembly that provides an appropriate rate of retrograde flow at a treatment site to direct dislodged particles into a catheter for efficient removal, without damaging the treatment vessel.

It is a further object of the present invention to provide a proximal catheter assembly that provides an external suction/infusion port that selectively may be used, in conjunction with natural aspiration techniques, to further influence flow in a treatment vessel.

It is yet a further object of the present invention to provide a proximal catheter assembly that allows emboli to be filtered and blood reperfused into a patient's vessel to reduce blood loss.

It is a further object of the present invention to provide a proximal catheter assembly that is configured to minimize "back-bleed" that occurs through a hemostatic port disposed at the proximal end of a catheter.

It is another object of the present invention to provide a proximal catheter assembly having a check valve functionality to selectively enable the provision of either natural or suction assisted aspiration through a working lumen of a catheter.

It is yet another object of the present invention to provide a proximal catheter assembly having a relief valve functionality to regulate the rate of suction-assisted aspiration that may be provided through the working lumen of the catheter.

These and other objects of the present invention are accomplished by providing a proximal catheter assembly that is configured to enable two types of aspiration through a catheter lumen. The proximal catheter assembly enables a substantially continuous rate of natural, physiologically-regulated aspiration through the catheter lumen using an arterial-venous shunt and, optionally, suction-assisted aspiration through the catheter lumen. This allows a physician to provide a substantially continuous rate of retrograde flow in a treatment vessel during a medical procedure, while providing an external suction/infusion port that selectively may be used to further influence the rate of aspiration within the vessel. In addition, the suction/infusion port may be used to selectively provide an antegrade flow, e.g., of a therapeutic drug or lytic agent.

In a first embodiment, a proximal catheter assembly of the device of the present invention comprises a handle that is coupled to a catheter, so that a working lumen of the catheter is in fluid communication with a bore of the handle. The handle preferably comprises an external suction/infusion port and at least one hemostatic port, each of which are in fluid communication with the working lumen of the catheter. The handle also is coupled to a blood outlet port that is in fluid communication with the working lumen, and preferably further comprises an inflation port that is in fluid communication with an inflation lumen of the catheter.

In use, the blood outlet port coupled to the handle may be coupled to a venous return line, which is adapted to be disposed in a remote vein. When the venous return line is disposed in the remote vein, and when an occlusive element of the catheter is deployed in a patient's artery, a pressure differential between venous and arterial pressure will cause blood to flow in a retrograde fashion in the artery. Specifically, blood in the artery flows into the working lumen, through the outlet port, and then through the venous return line, where it then is reperfused into the remote vein. A filter may be disposed between the outlet port and the venous return line to remove any emboli prior to reperfusing blood into the remove vein.

This natural, physiologically-regulated aspiration through the outlet port coupled to the catheter handle preferably occurs before, during and after a medical procedure performed through the working lumen of the catheter to effectively remove thrombi and/or emboli from the vessel. Additional suction selectively may be applied by coupling a syringe to the external suction/infusion port, to further influence aspiration of the vessel. Alternatively, the syringe may be used to infuse saline, drugs or other therapeutic agents to the treatment site. The hemostatic port coupled to the handle allows for the delivery of angioplasty, stent delivery systems or other devices to the treatment site.

In an alternative embodiment of the present invention, the proximal catheter assembly further comprises a handle having a roller clamp valve. The roller clamp valve may be used to selectively inhibit flow through the handle, so that "backbleed" from the catheter lumen through the hemostatic port is reduced.

In a preferred embodiment of the present invention, a proximal catheter assembly is provided that comprises a check/relief valve configured to perform functions associated with conventional check valves and relief valves. The check valve functionality allows the valve to regulate the direction of fluid flow by selectively enabling either natural or suction assisted aspiration through a working lumen of a catheter. The relief valve functionality allows the valve to regulate the rate of suction-assisted aspiration that may be provided through the working lumen of the catheter. When the rate of suction-assisted aspiration exceeds a predetermined threshold, the check/relief valve opens to allow blood to be drawn from tubing coupled to the venous return line. Using this technique, relatively high rates of suction-assisted aspiration will not be imposed upon the working lumen and the patient's vessel, but rather will be mitigated by the check/relief valve.

BRIEF DESCRIPTION OF THE DRAWINGS

Further features of the invention, its nature and various advantages will be more apparent from the accompanying drawings and the following detailed description of the preferred embodiments, in which:

FIG. 1 provides a top sectional view of a proximal catheter assembly in accordance with principles of the present invention;

FIG. 2 provides a cross-sectional view along line A—A of FIG. 1;

FIGS. 3A–3B are, respectively, a top view and a top sectional view of an alternative embodiment of the present invention;

FIGS. 4A–4C are, respectively, a side view and side sectional views of the proximal catheter assembly of FIGS. 3;

FIGS. 5A–5C are, respectively, two top views and a cross-sectional view illustrating a proximal catheter assembly having a check/relief valve provided in accordance with principles of the present invention;

FIGS. 7A–7B are, respectively, top and cross-sectional views illustrating an alternative embodiment of the check/relief valve of FIGS. 5A–6C; and FIGS. 8A–8C illustrate a method of using the check/relief valve of FIGS. 7A–7B.

DETAILED DESCRIPTION OF THE INVENTION

Figure 6A:
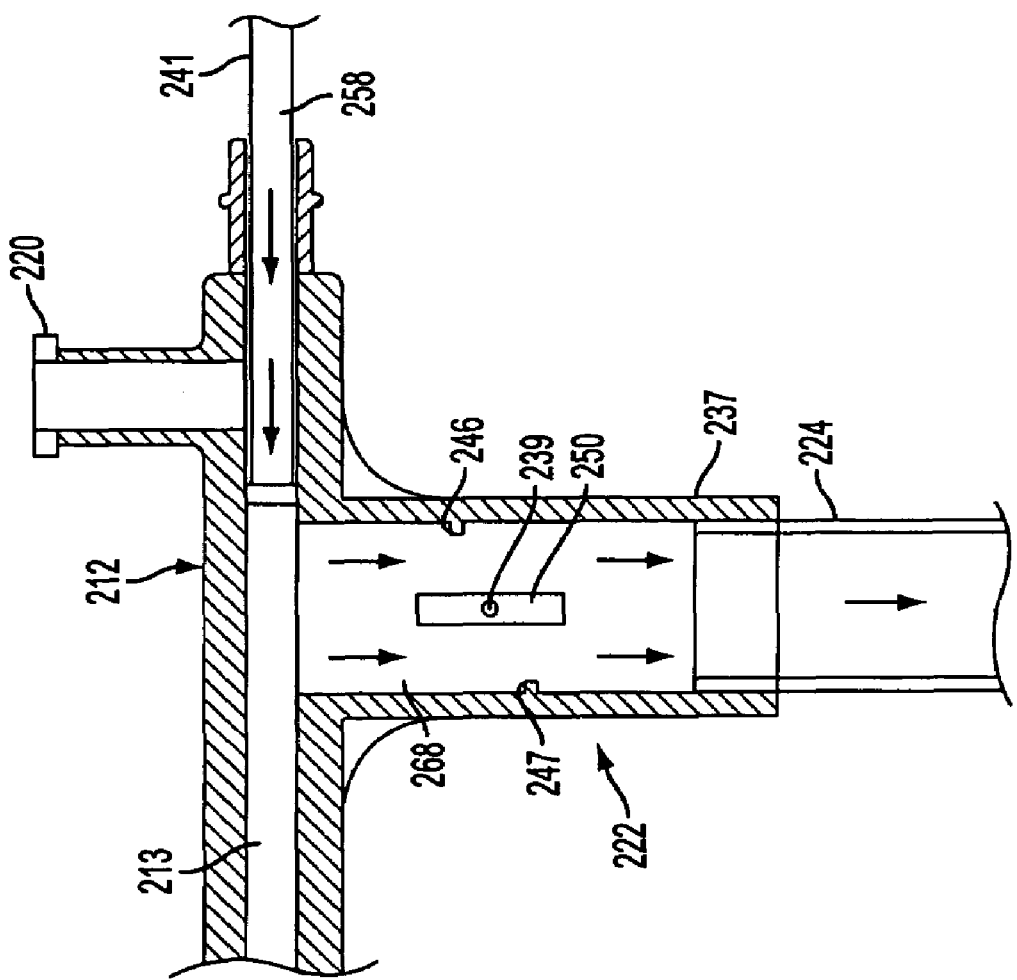
FIGS. 6A–6C illustrate a method of using the check/relief valve of FIGS. 5A–5C.

The present invention is directed to a proximal catheter assembly that is configured to enable natural aspiration through a catheter lumen and, optionally, suction-assisted aspiration or infusion through the catheter lumen. The proximal catheter assembly of the present invention enables a substantially continuous rate of natural, physiologically-regulated aspiration through the lumen of the catheter by enabling fluid communication between the lumen of the catheter and a patient's venous vasculature. The proximal catheter assembly also provides an external suction/infusion port that may be used in conjunction with a syringe, so that a physician further may influence the rate of aspiration through the lumen of the catheter. The provision of substantially continuous retrograde flow and, optionally, selectively increased rates of retrograde flow at a treatment site facilitates removal of emboli during an interventional procedure while minimizing trauma to the treatment vessel. The proximal catheter assembly preferably is provided with a check/relief valve configured to selectively provide either natural or suction assisted aspiration through the lumen, and further configured to regulate the rate of suction-assisted aspiration that may be provided through the lumen.

Referring now to FIG. 1, a top sectional view of a proximal catheter assembly constructed in accordance with principles of the present invention is described. Proximal catheter assembly 10 is coupled to catheter 41 having proximal and distal ends and working lumen 58 extending therebetween. Proximal catheter assembly 10 comprises handle 12 having proximal and distal ends, and bore 68 extending therebetween. The proximal end of catheter 41 preferably is affixed within bore 68 near distal end 13 of handle 12, so that working lumen 58 of catheter 41 and bore 68 of handle 12 are in fluid communication with each other.

Handle 12 comprises external suction/infusion port 14, which is in fluid communication with bore 68 and working lumen 58 of catheter 41. External suction/infusion port 14 is configured to receive syringe 16, which may be used to induce enhanced aspiration or infusion through working lumen 58.

Handle 12 preferably further comprises inflation port 20, which is in fluid communication with inflation lumen 63 of catheter 41. Inflation lumen 63 further is in fluid communication with occlusive element 42, e.g., a balloon that is disposed at the distal end of catheter 41, so that occlusive element 42 may be deployed via inflation port 20 and inflation lumen 63.

Handle 12 is coupled to blood outlet port 26, which in turn preferably is coupled to a venous return line (not shown) that is adapted to be inserted into a patient's venous vasculature. In one embodiment, one-way check valve 22 may be disposed between handle 12 and blood outlet port 26, as shown in FIG. 1, to ensure that flow through the valve occurs exclusively in the direction indicated. For example, when flow is aspirated through catheter 41 via working lumen 58, that flow may enter and pass through one-way check valve 22, then flow through optional tubing 24 and through blood outlet port 26. However, one-way check valve 22 will not allow flow to occur through the valve in an opposite direction, i.e., from blood outlet port 26 into working lumen 58. For example, one-way check valve 22 may close when suction is being provided via syringe 16 to ensure that flow from blood outlet port 26 does not re-enter bore 68 and/or working lumen 58.

Handle 12 of proximal catheter assembly 10 further is coupled to at least one hemostatic port 18, e.g., a Touhy-Borst connector, which is per se known in the art. Hemostatic port 18, bore 68 and working lumen 58 of catheter 41 are sized to permit the advancement of conventional angioplasty catheters, stent delivery systems, thrombectomy systems, and other devices to a vascular treatment site via working lumen 58.

In accordance with principles of the present invention, proximal catheter assembly 10 may be used in conjunction with catheter 41 during a medical procedure to provide a substantially continuous rate of natural, physiologically-regulated aspiration through working lumen 58 and, optionally, suction-assisted aspiration.

During the medical procedure, catheter 41 may be disposed in a patient's artery and occlusive element 42 may be deployed. The natural aspiration may be provided through working lumen 58 when a venous return line (not shown), which is coupled to blood outlet port 26, is introduced into a remote vein. Once this arterial-venous circuit is established, negative pressure in the venous line during diastole will establish a low rate continuous flow of blood through working lumen 58 of catheter 41, to the patient's vein via the venous return line. In effect, this arterial-venous shunt allows blood flow in the patient's artery that is distal of occlusive element 42 to flow in a retrograde fashion through working lumen 58, through one-way check valve 22, through outlet port 26, through the venous return line and back into the remote vein. This method, which utilizes the difference between venous and arterial pressure, may be used to provide a substantially continuous rate of aspiration at a treatment site before, during and after a medical procedure, to ensure that emboli generated during the medical procedure are directed into working lumen 58 for safe removal. A filter (not shown) may be coupled between blood outlet port 26 and the venous return line so that emboli may be removed and filter blood reperfused into the venous vasculature.

With retrograde flow established in the selected artery via the venous return line, a medical procedure may be performed through hemostatic port 18 and working lumen 58. At any time before, during or after the medical procedure, additional suction-assisted aspiration may be provided at the treatment site via syringe 16. It is preferred that the additional suction provided by syringe 16 only is used in conjunction with the above-described natural aspiration technique for a limited period of time, e.g., at the time a vascular lesion is being traversed or disrupted, to ensure that trauma to the vessel wall due to the external suction is reduced. Alternatively, syringe 16 may be used to temporarily establish antegrade flow, e.g., to infuse contrast agents, drugs, lytic agents or other therapeutic agents.

Referring now to FIG. 2, a cross-section view along section A—A of FIG. 1 is provided. As shown in FIG. 2, catheter 41, which may be used in conjunction with proximal catheter assembly 10, preferably comprises inner layer 60 covered with a layer of flat stainless steel wire braid 61 and polymer cover 62. Inflation lumen 63 is disposed within polymer cover 62 and couples inflation port 20 to occlusive element 42. A proximal end of working lumen 58 is in fluid communication with external suction/infusion port 14, hemostatic port 18, and blood outlet port 26, as described hereinabove with respect to FIG. 1.

Referring now to FIGS. 3, an alternative proximal catheter assembly constructed in accordance with principles of the present invention is described. FIG. 3A provides a top view of proximal catheter assembly 100, which is coupled to catheter 141 having proximal and distal ends and working lumen 158 extending therebetween. Catheter 141 preferably is provided in accordance with catheter 41 of FIGS. 1–2.

Proximal catheter assembly 100 preferably comprises handle 110 and hub 112, each having proximal and distal ends. The distal end of hub 112 is configured to receive and sealingly engage the proximal end of catheter 141, as shown in a top sectional view in FIG. 3B. Working lumen 158 of catheter 141 is in fluid communication with bore 113 of hub 112, which in turn is in fluid communication with lumen 136 of tubing 135, as described in detail with respect to FIG. 4 hereinbelow.

Proximal catheter assembly 100 further comprises inflation port 120, which preferably is coupled to hub 112 and is in fluid communication with an inflation lumen of catheter 141, e.g., inflation lumen 63 of FIG. 1. The inflation lumen of catheter 141 further is in fluid communication with occlusive element 142 disposed at the distal end of catheter 141, so that occlusive element 142 may be deployed via inflation port 120 and the inflation lumen.

Hub 112 of proximal catheter assembly 100 further is coupled to blood outlet port 126, which in turn is coupled to a venous return line (not shown) that is adapted to be inserted into a patient's venous vasculature, as described hereinabove. In a preferred embodiment, one-way check valve 122 is disposed between distal hub 112 and blood outlet port 126 to ensure that flow through one-way check valve 122 occurs only in the direction indicated. As shown in FIG. 3B, one-way check valve 122 preferably comprises ball 123 that is configured to plug an opening of one-way check valve 122, if necessary, to prevent flow from occurring from outlet port 126 into bore 113 and/or working lumen 158.

External suction/infusion port 114 is in fluid communication with working lumen 158 of catheter 141, as shown in FIGS. 4B–4C. External suction/infusion port 114 is configured to provide external suction through working lumen 158 when a syringe is coupled to port 114. Alternatively, as described hereinabove with respect to port 14 of the embodiment of FIG. 1, port 114 may be used to infuse fluid into the vessel.

Handle 110 further comprises at least one hemostatic port 118 that is in fluid communication with working lumen 158 of catheter 141. Hemostatic port 118 and working lumen 158 are sized to permit the advancement of conventional angioplasty catheters, stent delivery systems, and thrombectomy systems to a vascular treatment site via working lumen 158. As shown in FIG. 3B, and also from side sectional views in FIGS. 4B–4C, handle 110 further comprises a section of tubing 135 that is disposed substantially within handle 110. Tubing 135 comprises lumen 136 that is in fluid communication with hemostatic port 118, external suction/infusion port 114, bore 113 of hub 112 and working lumen 158 of catheter 141.

Handle 110 further comprises roller clamp valve 129, which is configured to selectively inhibit flow through handle 110. Roller clamp valve 129 preferably comprises roller clamp 130 that is mounted on shaft 131, whereby shaft 131 is configured for longitudinal motion within angled slot 132, as shown from a top sectional view in FIG. 3B and from side sectional views in FIGS. 4B–4C. Angled slot 132 is disposed within a portion of handle 110 and tapers from a proximal point in which it is substantially adjacent to tubing 135, as shown in FIG. 4B, to a distal point in which it is further away from tubing 135, as shown in FIG. 4C.

When roller clamp 130 is provided in a distal position within angled slot 132, it will not inhibit fluid transfer occurring within lumen 136 of tubing 135, as shown in FIG. 4B. However, when roller clamp 130 is disposed in a proximal position within angled slot 132, as shown in FIG. 4C, it impinges upon tubing 135 and inhibits flow within lumen 136. In effect, roller clamp valve 129 serves as a switch that allows a physician to selectively inhibit fluid transfer between working lumen 158 of catheter 141 and hemostatic port 118. By inhibiting flow through lumen 136 of tubing 135, roller clamp valve 129 may prevent "backbleed" from occurring when hemostatic port 118 is open, e.g., when catheter 141 is advanced over a guidewire to a treatment site.

In accordance with principles of the present invention, proximal catheter assembly 100 then may be used in conjunction with catheter 141 during a medical procedure to provide a substantially continuous rate of natural aspiration and, optionally, syringe-assisted aspiration via external suction/infusion port 114. The preferred method for obtaining the substantially continuous rate of natural aspiration using proximal catheter assembly 100 is the same technique described hereinabove with respect to proximal catheter assembly 10 of FIG. 1, which disposes a venous return line in a remote vein and utilizes the difference between venous and arterial pressure to achieve retrograde flow at a treatment site.

Referring now to FIGS. 5A–6C, features of a multifunction check/relief valve provided in accordance with principles of the present invention are described. In FIG. 5A, proximal catheter assembly 200 preferably is constructed in accordance with proximal catheter assembly 100 of FIGS. 3A–4C, except as noted below. Proximal catheter assembly 200 is coupled to catheter 241 having proximal and distal ends and working lumen 258 extending therebetween. Catheter 241 preferably is constructed as described hereinabove with respect to catheter 41 of FIGS. 1–2.

Proximal catheter assembly 200 preferably comprises handle 210 and hub 212, each having proximal and distal ends. Working lumen 258 of catheter 241 is in fluid communication with bore 213 of hub 212, which is turn is in fluid communication with handle 219, as described hereinabove with respect to the embodiment of FIGS. 3–4. Handle 210 preferably further comprises inflation part 220. Hub 212 of proximal catheter assembly 200 further is coupled to tubing 224, which in turn preferably is coupled to a venous return line (not shown) that is adapted to be inserted into a patient's venous vasculature, as described hereinabove.

External suction/infusion port 214 is in fluid communication with working lumen 258 of catheter 241, as described in FIGS. 4B–4C hereinabove. External suction/infusion port 214 is configured to provide external suction through working lumen 258 when a syringe is coupled to port 214. Alternatively, port 214 may be used to infuse fluid into a vessel.

In the embodiment of FIG. 5A, check/relief valve 222 is disposed within hub 212 and configured to perform functions associated with conventional check valves and relief valves, as described in FIGS. 6A–6C hereinbelow. Alternatively, it will be apparent to those of skill in the art that check/relief valve 222 may be provided as a separate component, i.e., not disposed within hub 212, so long as valve 222 is in fluid communication with tubing 224, working lumen 258, and external suction/infusion port 214 via bore 213.

Referring now to FIG. 5B, a detailed top sectional view of check/relief valve 222 of FIG. 5A is provided. Check/relief valve 222 preferably comprises frame 250 and at least one flap 252 affixed to interior surface 257 of frame 250, as shown in FIG. 5C from a cross-sectional view along line B—B of FIG. 5B. A plurality of distinct, adjacent flaps 252 may be provided that are configured to be sealingly engaged with each other, as shown in FIG. 5C. Alternatively, membrane 261 may be affixed about its perimeter to interior surface 257 of frame 250, whereby flaps 252 are formed from at least one lateral or longitudinal slit 253 disposed in membrane 261. In a preferred embodiment, four flaps 252 are formed from membrane 261 when orthogonal slits 253 are cut into the membrane, as illustrated in FIG. 5C.

Check/relief valve 222 preferably comprises a circular configuration and is disposed within valve housing 237 of hub 212, which also preferably comprises a circular configuration. It is desirable that exterior surface 258 of frame 250 comprises a diameter that is slightly smaller than the diameter of interior surface 259 of valve housing 237, as shown in FIG. 5C, so that an insignificant amount of fluid is permitted to flow therebetween.

Check/relief valve 222 preferably further comprises first and second pivot pins 239 and 240, which are affixed to opposing ends of frame 250, as shown in FIG. 5C. First and second pivot pins 239 and 240 are disposed within first and second bores 244 and 245 of valve housing 237, respectively. This permits frame 250 to rotate with respect to valve housing 237.

Referring back to FIG. 5B, check/relief valve 222 preferably further comprises proximal and distal stops 246 and 247 that extend radially into channel 268 of valve housing 237. Proximal and distal stops 246 and 247 inhibit rotation of frame 250 with respect to valve housing 237, for purposes described hereinafter.

Figure 6B:
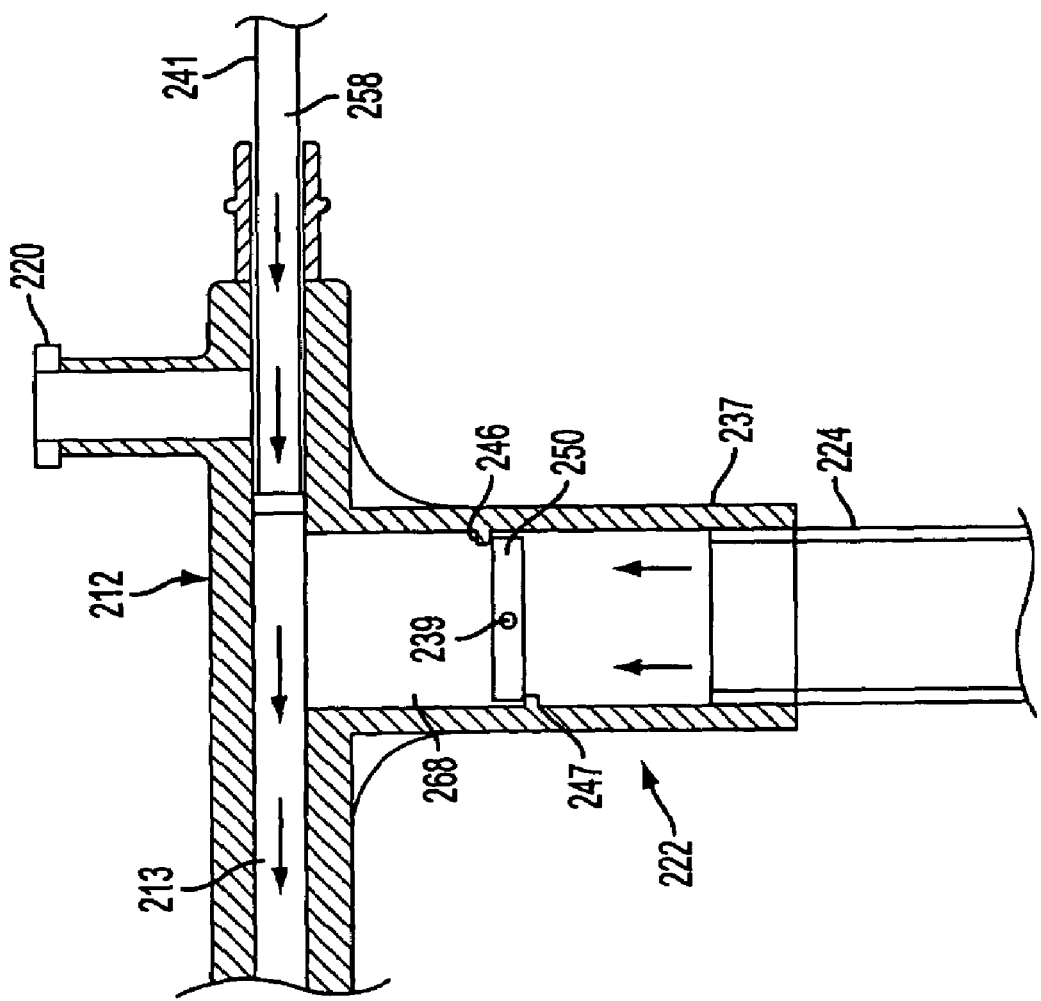
Figure 6C:
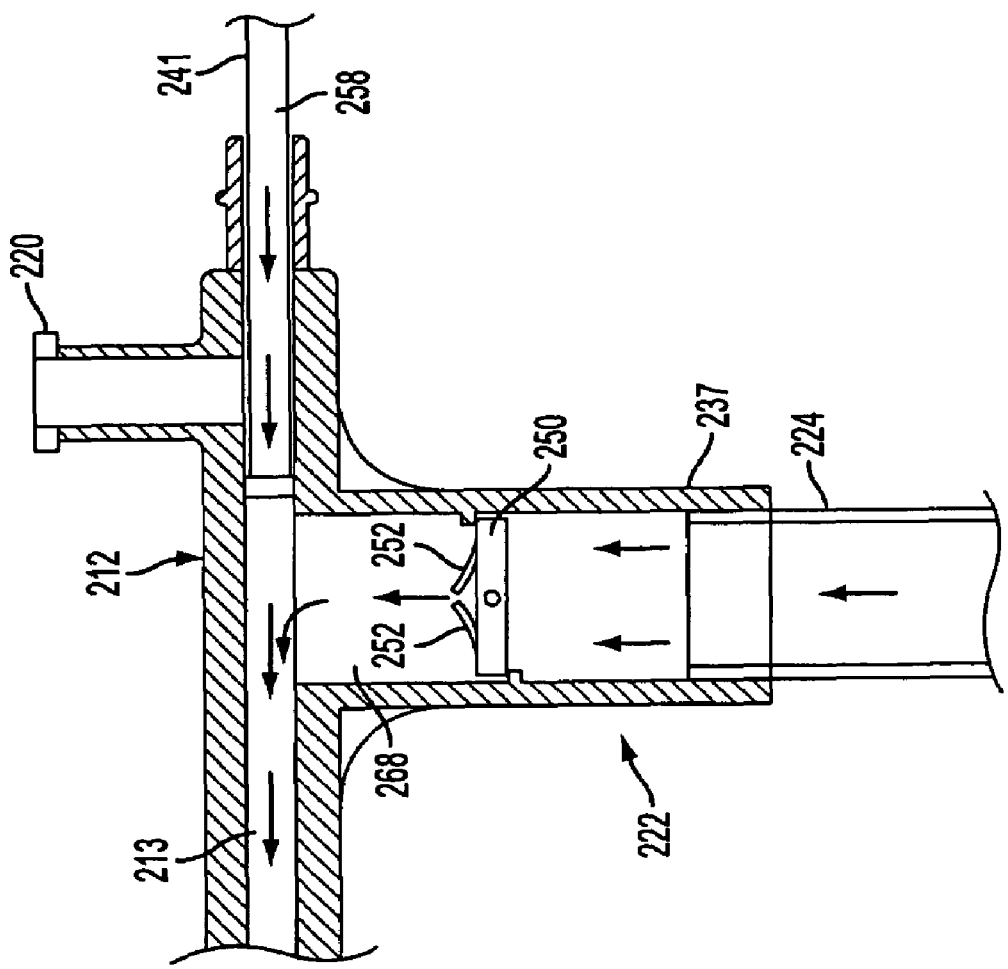

Referring now to FIGS. 6A–6C, a preferred method for using check/relief valve 222 is provided. In FIG. 6A, the arrows indicate the direction in which blood flows when the natural, physiologically-regulated flow is provided through working lumen 258 of catheter 241. Specifically, in a preferred embodiment, catheter 241 is disposed in a patient's artery and occlusive element 42 of FIG. 1 may be deployed.

Natural aspiration may be established through working lumen 258 when a venous return line (not shown), which is coupled to tubing 224, is introduced into a remote vein. Once this arterial-venous circuit is established, negative pressure in the venous line during diastole will establish a low rate continuous flow of blood through working lumen 258 of catheter 241, to the patient's vein via the venous return line. In effect, this arterial-venous shunt allows blood flow in the patient's artery that is distal of occlusive element 42 to flow in a retrograde fashion through working lumen 258, through channel 268 of valve 222, into tubing 224, through blood outlet port 26 of FIG. 1, through the venous return line and back into the remote vein. A filter (not shown) may be coupled between blood outlet port 26 of FIG. 1 and the venous return line so that emboli may be removed and filtered blood reperfused into the venous vasculature.

During the period in which a relatively low rate of natural, physiologically-regulated flow is provided through tubing 224, check/relief valve 222 assumes an "open position" wherein frame 250 is substantially parallel to blood flow, as shown in FIG. 6A. In the open position, check/relief valve 222 functions as a conventional check valve by permitting the flow of blood and emboli exclusively in the direction indicated, i.e., fluid is permitted to flow around frame 250 and into tubing 224.

Referring now to FIG. 6B, operation of check/relief valve 222 is described where a physician applies a relatively low or moderate rate of suction-assisted aspiration via external suction/infusion port 214, e.g., using a syringe. The suction-assisted aspiration causes flow to occur in the direction indicated by the arrows in FIG. 6B. Suction-assisted aspiration through bore 213 causes frame 250 of check/relief valve 222 to rotate about pivot pins 239 and 240 until the frame contacts proximal and distal stops 246 and 247. Continued suction-assisted aspiration through bore 213 holds check/relief valve 222 in this "closed position," so that frame 250 is substantially orthogonal to fluid flow through channel 268.

In the closed position, check/relief valve 222 functions as a conventional check Valve by inhibiting flow through channel 268 when suction-assisted aspiration is applied via port 214. This feature of check/relief valve 222 serves to ensure that the desired rate of suction-assisted aspiration is imposed upon the patient's vessel via working lumen 258, instead of aspirating fluid from tubing 224 and the venous return line.

When the rate of suction-assisted aspiration is below a predetermined threshold, i.e., a level that generally will not cause damage to a patient's vessel, flaps 252 of check/relief valve 222 are substantially sealingly engaged with adjacent flaps to inhibit fluid flow through frame 250. In the closed state, the suction force imposed upon flaps 252 by external suction/infusion port 214 does not overcome the rigidity of flaps 252.

Referring now to FIG. 6C, when a relatively high rate of suction-assisted aspiration is applied via external suction/infusion port 214, flaps 252 of check/relief valve 222 assume an "open state," i.e., they no longer sealingly engage adjacent flaps. Instead, flaps 252 temporarily are drawn toward bore 213 by the excessive suction force, as shown in FIG. 6C. This forms a gap between adjacent flaps 252 and allows blood to flow between tubing 224 and bore 213 via channel 268, as indicated by the arrows in FIG. 6C.

In the open state of FIG. 6C, check/relief valve 222 functions as a conventional relief valve when the rate of suction-assisted aspiration exceeds a predetermined threshold. The relief feature of check/relief valve 222 allows blood to be partially drawn from tubing 224 and the venous line, which reduces the blood drawn from working lumen 258 and the patient's vessel. By mitigating the rate of excessively high suction-assisted aspiration imposed on the patient's vessel using check/relief valve 222, damage to the patient's vessel can be reduced.

When the rate of suction-assisted aspiration is reduced below the predetermined threshold, flaps 252 of check/relief valve 222 transition from the open state of FIG. 6C to the closed state of FIG. 6B. This allows the desired rate of aspiration to be imposed exclusively upon working lumen 258. Additionally, when suction-assisted aspiration is no longer applied, check/relief valve 222 automatically transitions from the closed position of FIG. 6B to the open position of FIG. 6A to re-establish natural aspiration via tubing 224 and the venous line.

The rigidity of flaps 252 preferably is proportional to a predetermined aspiration threshold rate and may be tailored for each particular intervention. The rigidity of flaps 252 may be established or varied by varying the material properties of membrane 261. Additionally, varying the size and configuration of slits 153 may vary the rigidity of flaps 252 to define the desired aspiration threshold.

It also will be appreciated by those skilled in the art that check/relief valve 222 of the present invention may be used when apparatus 200 exclusively has a potential for suction-assisted aspiration, and is not capable of the natural, physiologically-regulated aspiration described hereinabove. In this case, for example, tubing 224 may be coupled to a fluid source, e.g., saline, in lieu of being coupled to the venous return line or the atmosphere. Then, saline will be drawn through tubing 224, into channel 268 and through bore 213 to mitigate the suction-assisted aspiration rate imposed within working lumen 258.

Referring now to FIGS. 7–8, an alternative embodiment of check/relief valve 222 is described. In FIG. 7A, check/relief valve 322 comprises frame 350 and flaps 352, which preferably are provided in accordance with frame 250 and flaps 252 of FIGS. 5–6, respectively. However, in the embodiment of FIGS. 7–8, frame 350 comprises hinge 339 in lieu of pivot pins 239 and 240. Additionally, valve housing 337 preferably comprises inner ring 347 having aperture 348, in lieu of proximal and distal stops 346 and 347.

Referring to FIG. 7B, a cross-sectional view along line C—C of FIG. 7A is provided. Frame 350 preferably comprises a circular configuration having enlarged side region 338. Enlarged side region 338 may be coupled to hinge 339, e.g., a rod that is configured for rotational motion with respect to bore 345 of valve housing 337. It will be apparent to those skilled in the art that hinge 339 may comprise any suitable hinge that permits rotation of frame 350 between the positions depicted in FIGS. 8A–8B, for purposes described hereinafter.

Referring now to FIGS. 8, the operation of check/relief valve 322 is described, and is substantially similar to the operation of check/relief valve 222 of FIGS. 6A–6C. Specifically, in a preferred embodiment, catheter 341 is disposed in a patient's artery and occlusive element 42 of FIG. 1 is deployed. Natural aspiration may be provided through working lumen 358 when a venous return line (not shown), which is coupled to tubing 324, is introduced into a remote vein, as described hereinabove.

During the period in which a relatively low level of natural, physiologically-regulated flow is provided through tubing 324, valve 322 is provided in an "open position," whereby frame 350 is substantially parallel to blood flow, as shown in FIG. 8A. In the open position, frame 350 does not substantially impede blood flow through channel 368.

Referring now to FIG. 8B, when a physician applies a relatively low or moderate rate of suction-assisted aspiration via an external suction/infusion port coupled to bore 313, the suction-assisted aspiration causes flow in channel 368 to be directed toward bore 313. The suction force causes check/relief valve 322 to transition to a "closed position," as shown in FIG. 8B, whereby frame 350 rotates via hinge 339 to impede fluid flow through channel 368. The rotation of frame 350 is limited by inner ring 347, so that frame 350 is held substantially orthogonal to flow though channel 368.

In the closed position, check/relief valve 322 functions as a conventional check valve to ensure that fluid is not drawn from tubing 324, when the rate of suction-assisted aspiration is below a predetermined threshold, but rather from the patient's vessel via working lumen 358, e.g., to remove emboli. When the rate of suction-assisted aspiration remains below the predetermined threshold, check/relief valve 322 remains in a "closed state," whereby flaps 352 are substantially sealingly engaged with adjacent flaps to inhibit fluid flow through frame 350 and aperture 348.

Referring now to FIG. 8C, the rate of suction-assisted aspiration introduced via the external suction/infusion port exceeds a predetermined aspiration threshold. The excessively high rate of suction-assisted aspiration causes flow through bore 313 to exert a suction force upon frame 350 and flaps 352 that exceeds the predetermined rigidity of flaps 352. This causes check/relief valve 322 to assume an "open state," i.e., whereby flaps 352 are not sealingly engaged with adjacent flaps. Flaps 252 temporarily are drawn toward bore 213 by the excessive suction force, as shown in FIG. 8C, to form a gap between adjacent flaps 252. This allows fluid from tubing 324 to be drawn toward bore 313. As described hereinabove, this relief feature of check/relief valve 322 allows blood to be partially drawn from tubing 324 to mitigate the excessively high rate of aspiration imposed upon working lumen 358 and a patient's vessel.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Catheter assembly for regulating the rate of suction-assisted aspiration, the apparatus comprising:
   a hub having a distal end, a blood outlet port, an aspiration port, and a bore in fluid communication with the blood outlet port and the aspiration port;
   a catheter having a proximal end, a distal end, and a working lumen extending therebetween;
   wherein the distal end of the hub receives and is sealingly engaged with the proximal end of the catheter so that the bore is in fluid communication with the working lumen of the catheter, and
   a valve comprising a frame and at least one flap affixed to an interior surface of the frame in fluid communication with the working lumen of the catheter, the bore, the blood outlet and the aspiration port,
   wherein the valve is configured to regulate the direction of fluid flow between the working lumen of the catheter and the blood outlet port, and further to regulate the rate of suction-assisted aspiration provided by the aspiration port to the working lumen of the catheter.

2. The apparatus of claim 1 wherein the valve is configured to provide partial communication between the blood outlet port and the aspiration port when an aspiration threshold is exceeded.

3. The apparatus of claim 1, wherein the bore, and the working lumen are sized to permit the advancement of conventional angioplasty catheters, stent delivery systems, and thrombectomy systems to a treatment site distal to the catheter via the working lumen.

4. The apparatus of claim 1 wherein the frame comprises a circular configuration.

5. The apparatus of claim 4 wherein the frame is disposed within a valve housing having a circular configuration.

6. The apparatus of claim 1 further comprising at least one pivot pin coupled to the flame, the pivot pin configured to permit partial rotation of the frame with respect to a valve housing.

7. The apparatus of claim 6 further comprising proximal and distal stops coupled to an interior surface of the valve housing, the proximal and distal stops configured to limit rotation of the frame.

8. The apparatus of claim 1 further comprising at least one hinge coupled to the frame, the hinge configured to permit partial rotation of the frame with respect to a valve housing.

9. The apparatus of claim 8 further comprising an inner ring coupled to an interior surface of the valve housing, the inner ring configured to limit rotation of the frame with respect to the valve housing.

10. The apparatus of claim 1 wherein the flaps are formed from a membrane having at least one slit.

11. The apparatus of claim 1 wherein the flaps are provided with a predetermined rigidity.

12. The apparatus of claim 1 wherein the valve comprises an open position that enables flow from the working lumen to the blood outlet port, and a closed position that inhibits flow between the working lumen and the blood outlet port when suction is applied via the aspiration port.

13. The apparatus of claim 3, wherein the catheter further includes a single inflatable member, the inflatable member located on the distal end of the catheter.

14. A method for regulating the rate of suction-assisted aspiration provided to a working lumen of a catheter, the method comprising:
   providing apparatus comprising a hub having a distal end, a blood outlet port, an aspiration port, and a bore in fluid communication with the blood outlet port and the aspiration port, the distal end of the hub coupled to a catheter having a working lumen extending from its proximal end to its distal end;
   providing a valve comprising at least one flap, having a predetermined rigidity in fluid communication with the working lumen of the catheter, blood outlet port and the aspiration port;
   using the valve to regulate the direction of fluid flow between the working lumen of the catheter and blood outlet port; and
   when a rate of suction-assisted aspiration provided by the aspiration port exceeds a predetermined threshold, transitioning the valve to an open state wherein fluid from the blood outlet port is directed through the valve and toward the aspiration port.

15. The method of claim 14 further comprising returning the valve to a closed state when the rate of suction-assisted aspiration is reduced below the predetermined threshold.

16. The method of claim 14 wherein using the valve to regulate the direction of fluid flow comprises enabling fluid flow from the working lumen of the catheter into the blood outlet port when suction-assisted aspiration is not provided via the aspiration port.

17. The method of claim 14 wherein using the valve to regulate the direction of fluid flow comprises inhibiting fluid flow from the blood outlet port into the working lumen of the catheter when a rate of suction-assisted aspiration provided by the aspiration port is below the predetermined threshold.

18. The method of claim 14 wherein providing a valve comprises providing apparatus wherein the predetermined rigidity of the flap is proportional to the predetermined threshold.

19. The method of claim 14 further comprising varying the predetermined rigidity of the flap by varying the material properties of the flap.

20. The method of claim 14 further comprising varying the predetermined rigidity of the flap by varying the configuration of the flap.

21. The method of claim 14, wherein the bore and the working lumen are sized to permit the advancement of conventional angioplasty catheters, stent delivery systems, and thrombectomy systems to a treatment site distal to the catheter via the working lumen.

22. The method of claim 21, wherein the catheter further includes a single inflatable member, the inflatable member located on the distal end of the catheter.

* * * * *

UNITED STATES PATENT AND TRADEMARK OFFICE
CERTIFICATE OF CORRECTION

PATENT NO. : 7,004,931 B2 Page 1 of 1
DATED : February 28, 2006
INVENTOR(S) : Michael Hogendijk It is certified that error appears in the above-identified patent and that said Letters Patent is hereby corrected as shown below:

Column 12,
Line 16, "flame" should read -- frame --.

Signed and Sealed this

Ninth Day of May, 2006

JON W. DUDAS
*Director of the United States Patent and Trademark Office*